United States Patent [19]

Christophliemk et al.

[11] 4,255,549

[45] Mar. 10, 1981

[54] PROCESS FOR PREPARING ORGANOSILAZANES

[75] Inventors: Peter Christophliemk, Düsseldorf; Riza N. Oezelli, Neuss; Guenther Tischbirek, Düsseldorf, all of Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 60,277

[22] Filed: Jul. 25, 1979

[30] Foreign Application Priority Data

Aug. 3, 1978 [DE] Fed. Rep. of Germany ....... 2834027

[51] Int. Cl.$^3$ ............................................. C08G 77/04
[52] U.S. Cl. ..................................... 528/28; 427/387; 428/447; 428/450; 556/410
[58] Field of Search ................... 260/448.2 N; 528/28; 428/447, 450; 427/387

[56] References Cited

U.S. PATENT DOCUMENTS

| | | | |
|---|---|---|---|
| 2,564,674 | 8/1951 | Cheronis | 260/448.2 N |
| 2,579,416 | 12/1951 | Cheronis | 260/448.2 N |
| 2,579,417 | 12/1951 | Cheronis | 260/448.2 N |
| 2,579,418 | 12/1951 | Cheronis | 260/448.2 N |
| 3,143,514 | 8/1964 | Boyer | 528/28 |

*Primary Examiner*—Melvyn I. Marquis
*Attorney, Agent, or Firm*—Hammond & Littell, Weissenberger and Muserlian

[57] ABSTRACT

This invention is directed to an improved process for the preparation of condensable, film-forming organosilazanes by ammonolysis of organohalosilanes with liquid ammonia, the improvement comprising reacting a from about 5 to 15% by weight solution of organohalosilane in inert solvent with excess liquid ammonia under pressure at temperatures between 0° and 50° C.

12 Claims, No Drawings

PROCESS FOR PREPARING ORGANOSILAZANES

FIELD OF THE INVENTION

This invention concerns an improved process for the preparation of condensable, film-forming organosilazanes by ammonolysis of organohalosilanes.

BACKGROUND OF THE INVENTION

Organosilazanes are compounds having the general formula $R_nSi(NH_2)_{4-n}$ wherein R represents a monovalent hydrocarbon radical and n is 1, 2, or 3. The compounds can be obtained best by reacting corresponding organohalosilanes of formula $R_nSiX_{4-n}$, wherein R and n are as described above and X is a halogen atom, with ammonia, a process referred to as "ammonolysis." In the process, the halogen atoms are substituted in the first reaction step by $NH_2$-groups, and then the halide-ions react with excess ammonia to form ammonium halide, which is immediately precipitated with a suitable solvent so that it does not take part in the reaction. Thus, two molecules of ammonia are required to replace one halogen atom.

The preparation of condensable silazanes by ammonolysis of the corresponding halogen silanes has been described by Nicholas D. Cheronis in U.S. Pat. Nos. 2,564,674, 2,579,416, and 2,579,418, all of which are incorporated herein by reference. According to these patents, ammonolysis was carried out with gaseous or liquified ammonia under atmospheric, or normal, pressure.

In ammonolysis with gaseous ammonia, the ammonia is passed, i.e., bubbled, through a solution of the organohalosilane. Depending on the temperature of the solution and the rate of introduction, considerable losses of ammonia are incurred. In addition, significant amounts of solvent are carried away with the ammonia. These losses are not only uneconomical, but they also lead to pollution of the environment.

These losses can be avoided to a great extent in ammonolysis with gaseous ammonia under normal pressure only if the reaction is carried out at temperatures far below the evaporation temperature of ammonia, $-33.4°$ C. Even with smaller batches, reaction temperatures of about $-40°$ to $-60°$ C. must be maintained to prevent sudden temperature increases, due to the introduction of excessive amounts of ammonia, and local temperature fluctuations. Beyond that, there is always the acute danger in ammonolysis with gaseous ammonia that the gas feed pipes will be clogged by ammonium halide deposits. Ammonolysis under normal pressure with preliquified ammonia has the disadvantage of raising cooling problems.

The reaction of organohalosilanes with liquid ammonia—whether the ammonia is pre-liquified or liquified in the solution—always requires temperatures below $-40°$ C. under normal pressure. To attain and maintain these low temperatures, elaborate cooling units and special insulating measures are required. The energy consumption for this type of cooling is high. Beyond that, the low temperatures and the great temperature fluctuations lead to rapid fatigue of the equipment employed, and the reaction vessels and associated equipment have only a short service life.

OBJECTS OF THE INVENTION

It is an object of this invention to provide an improved process for the production of organosilazanes.

It is also an object of this invention to provide an improved process for the production of condensable, film-forming organosilazanes by ammonolysis of organohalosilanes.

These and other objects of the invention will become more apparent in the discussion below.

DETAILED DESCRIPTION OF THE INVENTION

It has been found that the ammonolysis of organohalosilanes can be carried out in a much safer and more economical manner. According to Applicants' invention condensable, film-forming organosilazanes are prepared by ammonolysis of organohalosilanes with liquid ammonia wherein a from about 5 to 15% by weight solution of organohalosilanes in inert solvent is reacted with liquid ammonia in excess under pressure at temperatures above $0°$ C. and below $50°$ C.

It is advantageous to carry out the reaction with a great excess of ammonia, at least a three-fold, and preferably a four to six-fold, amount by weight, as compared to the weight of the organohalosilane.

To maintain a uniform reaction course, and to thus avoid local overheating and, particularly, to eliminate the considerable heat of reaction, it is advisable to effect the ammonolysis in a suitable solvent. Since the silicon-halogen-bonds hydrolyze immediately under the action of water or hydroxyl-ions, the solvent should be substantially anhydrous to avoid yield losses.

Preferably, inert solvents are used since, with regard to subsequent application of the products, these react neither with the organohalosilane nor with the organosilazane. Also, preferred solvents will have a low vapor pressure. However, if the solvent evaporates too slowly, i.e., if the vapor pressure is too low, higher temperatures must be applied later to obtain suitable films. Useful organic solvents include alicyclic or aliphatic hydrocarbon ethers having 4 to 8 carbon atoms and unsubstituted aromatic hydrocarbons having 6 to 8 carbon atoms or chlorinated hydrocarbons having 1 to 6 carbon atoms, such as diethyl ether, dioxane, benzene, toluene, benzine, chlorobenzene, carbon tetrachloride, chloroform, trichlorofluoromethane, 1,1,2-trichlorofluoroethane, and, particularly, methylene chloride.

The order of the addition when mixing ammonia with the organohalosilane-solution is not critical. However, it is advantageous to charge the autoclave used with the organohalosilane solution and then to add liquid ammonia. If necessary, the liquid ammonia can also be diluted with inert solvents. This procedure is of particular interest when the excess ammonia recovered is used again.

In general, it is sufficient to work under the intrinsic pressure of ammonia at the corresponding temperature. However, depending on the equipment, it may be advisable to increase the pressure in the reaction vessel slightly by feeding an inert gas, such as nitrogen. Suitable working pressures would include pressures under 50 bars.

It is advisable to work in the autoclave at room temperature and to cool with water. It is advantageous to continue the stirring for several hours after the organohalosilane has been mixed with ammonia, preferably for 3 to 12 hours, under pressure. An expedient procedure is described below:

A closable reaction vessel with cooling water jacket, stirrer inlet and outlet connection, manometer, thermostat and safety valve, is charged with a solution of organohalosilane in an inert solvent, such as methylene chloride. The reaction vessel should be capable of operation at pressures of at least 50 bars although the internal pressure can be kept below 10 bars according to the process of the invention, even at temperature peaks of up to about 50° C. The reaction vessel is filled about half-way with a from about 5 to 15% by weight, preferably from about 8 to 10% by weight, solution of organohalosilane, and the solution is cooled by the cooling jacket, which has a cooling water temperature of from about 15° to 20° C. The ammonia required for the ammonolysis is fed from steel cylinders directly into a smaller coolable autoclave, and then pumped into the reaction vessel. In an alternate procedure, the ammonia can be fed or forced into the reaction vessel by use of an inert gas, such as nitrogen, at a pressure of from about 15 to 25 bars. The reaction mixture is stirred intensively during the entire reaction. Even with batch volumes of up to 150 liters, the ammonia can be added within ten minutes in such a way that the internal pressure rises to only slightly more than 10 bars. Brief temperature peaks of up to 50° C. may appear in the reaction chamber; however, with a slower addition of ammonia, particularly at the start of the ammonolysis, the inside temperature does not rise above 35° C. and the internal pressure does not rise above about 6 bars. After the entire quantity of ammonia has been added, the inside temperature drops rapidly, in response to the cooling water temperature, to below 20° C.

To complete the ammonolysis, the stirring is continued for several hours, e.g., 3 to 12 hours, under pressure and cooling. The excess ammonia is then distilled into the smaller autoclave by heating the reaction mixture to from about 40° to 50° C. Here, the use of a compressor with subsequent pressure cooling to improve the liquification of ammonia is particularly helpful. The distilled ammonia can be used again for subsequent batches. The composition of the distillate, as far as ammonia and the solvent are concerned, is first determined analytically by titration of the ammonia content.

After distillation of the excess ammonia and cooling of the reaction mixture, the mixture is allowed to expand and the precipitated ammonium halide is filtered off. To avoid yield losses, the precipitate is washed with some solvent and the filtrate and the wash liquors are combined. If necessary or desired, the wash liquor can also be used as a solvent for another batch. Depending on the intended application, the silazane solution thus obtained is further processed, usually by dilution with other, different inert solvents.

Virtually all organohalosilanes can be converted to corresponding silazanes by ammonolysis. Preferably organochlorosilanes are employed because they are readily available and economical. Especially preferred are mono- and diorganochlorosilanes of the general formula $R_nSiCl_{4-n}$ (n=1 or 2), which contain as hydrocarbon radicals R, which may be the same or different, linear or branched aliphatic groups $C_nH_{2n+1}$ with n=1 to 6, cyclohexyl, phenyl, or benzyl groups. In a diorganochlorosilane, different hydrocarbon groups R and R' can be adjacent, corresponding to the formula RR'SiCl$_2$. Methyl trichlorosilane and dimethyl dichlorosilane are particularly preferred organohalosilanes according to this invention.

The silazanes are readily condensed. (The terms "condensation", "cross-linkage", and "polymerization" are used here synonymously, as it is customary in the literature). Thus, mono-organohalosilanes $RSiX_3$ and diorganohalosilanes $R_2SiX_2$ react immediately, with the exception of silanes having particularly bulky hydrocarbon groups, after substitution of the halogen atoms by NH$_2$ groups in the solvent according to reaction equations (1) and (2) below, forming condensed silazanes without the intermediately formed monomeric silazanes "RSi(NH$_2$)$_3$" or "R$_2$Si(NH$_2$)$_2$" being isolated:

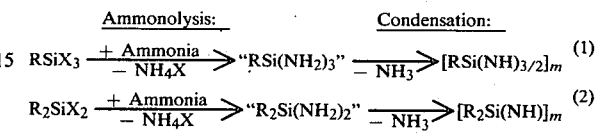

No data can be given for the size of m and thus for the degree of condensation, in solution. With the evaporation of the solvent, the degree of condensation increases constantly until the high-polymeric polysilazane film remains, and m assumes very high values.

The "monofunctional" triorganohalogen silanes $R_3SiX$ can only be dimerized to the corresponding disilazanes $R_3SiN(H)SiR_3$ after ammonolysis since there is only one linkage point on the silicon atom. Since the formation of a film requires a high cross-linking ability or capacity, the suitable organohalosilanes are the "difunctional" diorganohalosilazanes, with two linkage points, and particularly the "trifunctional" mono-organohalosilazanes, with three linkage points.

Polymeric diorganosilazanes contain primarily chains or rings with groupings of type

and polymeric monoorganosilazanes contain structures of the type

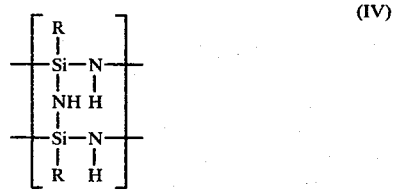

Polymeric organosilazanes, i.e., polysilazane, films can be obtained in a simple manner at room temperature already, by applying the silazane solution to a suitable substrate and allowing the solution to evaporate.

If the polysilazane film is to be formed at room temperature, highly volatile solvents are preferred, such as ethers or low-boiling (chlorinated and/or perfluorinated) hydrocarbons; however, if the film is to be applied to a hot substrate, the use of higher boiling solvents is recommended. Uniform evaporation of solvent can be ensured by a suitable solvent combination, which will depend on the application temperature. A particular concern is that too rapid evaporation of the solvent can considerably interfere with the formation of a film, and the resulting film has poorer application properties.

It has been found that the film formation is particularly good when the ammonolysis is effected with a great excess of ammonia. On a strictly stoichiometric basis, the ammonolysis would only require two molecules of ammonia per halogen atom; however, according to the invention, at least a three-fold, preferably a four to six-fold, amount by weight of ammonia, based on the organohalosilane, is desired. In the process of the invention, this great excess of ammonia can be practically completely recovered.

The film formation is furthermore particularly good when the stirring is continued for several hours under pressure after the mixing of organohalosilane and liquid ammonia is complete, while the cooling temperature is maintained. In addition, the ammonium halide, particularly ammonium chloride, is then obtained in a form which is easier to filter.

The ultimate suitability of a film for an intended application can only be determined under realistic conditions. However, as a preliminary test, a visual evaluation of the film quality can be made. To determine suitability, about 10 ml of the silazane solution are applied on a metal plate, and the solvent is allowed to evaporate at the application temperature. With a too low solids concentration of the silazane solution, the application must be repeated, if necessary. Disturbances of the film-formation and extraneous components, e.g., ammonium halide deposits, can be clearly recognized, particularly with alternating incidental light. The hardness and displaceability of the film can be judged by scoring the film, and the flexibility of the film can be judged by bending the plate.

A thin flexible steelplate is preferably used as a substrate for the film. After the film hardens at the application temperature, a so-called grid section is made by using a razor blade or a sharp knife to make four to six parallel cuts in a distance of 3 to 5 mm and then, perpendicularly above these cuts, the same number of parallel cuts. An adhesive tape is pasted on this grid section, and the tape is then torn off immediately. Only if the film is not torn off with the tape, that is, if it adheres firmly to the substrate, is the film substrate for use.

The flexibility test comprises bending the coated thin plate about a steel mandrel or a pipe. During this bending, the film should not crack off from the steel plate.

The films produced according to the invention have a uniform thickness, consistency, and surface quality. They are transparent and flexible and can be thermally stressed. Depending on the substrate, these films show excellent adhesive strength. These remarkable film properties permit the use of polysilazanes in, for example, the leather, textile, or plastic or rubber industry. For example, polysilazanes can be used to impart water repellency and other desirable properties to leather and textiles.

EXAMPLES

The following examples are intended to demonstrate the invention and are not to be construed as limiting the invention thereto.

EXAMPLE 1

A 200 liter pressure tank of refined steel with stirrer, cooling jacket (with inlet and outlet water connection), thermostat, manometer, and safety valve, was filled with 100 liters of methylene cloride and 10 kg of methyltrichlorosilane. The solution was cooled to 18° C. by means of the cooling jacket. A separate smaller pressure vessel of refined steel with jacket cooling (brine at 5° C.) was charged with 50 kg of liquid ammonia from steel cylinders.

After the desired weight of ammonia was charged to the smaller vessel, the ammonia was pressed, i.e., fed, with nitrogen (20 bars) through a pressure line into the large reaction vessel within 40 minutes. Both during the ammonolysis and during the after-reaction period, the reaction mixture was stirred thoroughly. During the addition of ammonia, the inside temperature rose to 48° C., and the internal pressure rose to 7.0 bars. After the addition of ammonia was complete, the inside temperature dropped again to 20° C. within 40 minutes, due to the continued stirring. The stirring was continued for four hours under pressure at 18° to 20° C., and then the excess ammonia was distilled off by employing hot water in the jacket to heat the reaction solution to 30° C. and using the small pressure vessel as a distillation receiver. Altogether 60 kg of distillate were collected, which distillate contained, according to titration, 66% by weight of ammonia and 34% by weight of methylene chloride.

After the distillation was complete and the reaction mixture was cooled to room temperature, the vessel was opened. The reaction mixture was filtered within a few minutes. The ammonium chloride deposit was washed with 10 liters of methylene chloride, and then the filtrate and the wash liquor were combined.

The monomethyl silazane solution thus obtained (130 kg) was clear and colorless and contained 3.0% by weight solids, after drying for three hours at 60° C. The yield was thus 94% of theoretical.

To evaluate film quality, 20 ml of the silazane solution were poured into an aluminum dish having a flat bottom. After evaporation of methylene chloride from the aluminum dish by standing at room temperature, a thin and uniformly smooth transparent film formed, no turbidities or other irregularities being present. The film was flexible and adhered firmly to the substrate. Even after the film was annealed for several hours at 150° C., the film properties remained unchanged.

COMPARISON EXAMPLE 1

As a comparison representing the state of the art, an ammonolysis procedure similar to that of Example 1, but using gaseous ammonia under normal pressure, was performed. The procedure was as follows:

Five liters of methylene chloride and 500 g of methyltrichlorosilane were fed via a reflux condenser into a 10 liter reaction vessel with stirrer, thermostat, gas inlet pipe, and gas outlet pipe. This silane solution was cooled by an outside cooling system with ice water to 5° C., and then ammonia was conducted under vigorous stirring and continued cooling (directly from the steel cylinder) through the silane solution in such a way that the inside temperature did not rise above 25° C. The excess ammonia was discharged over the reflux condenser. At the start of the ammonolysis, ammonia was weakly dosed; then, it was conducted in a strong stream through the solution. After the ammonia had been introduced for four hours and then cooled for four hours, the solution was filtered and the ammonium chloride precipitate was washed with 500 ml of methylene chloride. The filtrate and the wash liquor were combined.

The silazane solution (8.3 kg), which was clear and colorless similar to the solution in Example 1, contained 4.6% by weight solids (after drying for 3 hours at 60° C.). The yield was thus 91% of theoretical with much less solvent since solvent was carried away with the ammonia. A film produced using the procedure set forth in Example 1 showed a very non-uniform surface with "white" spots and uneven areas. In addition, small parts of the film could be torn off with adhesive tapes after the grid cuts. These films were inadequate for use.

EXAMPLE 2

Following the procedure of Example 1, 10 kg of n-propyltrichlorosilane in 100 liters of ethylenechloride were reacted with 50 kg ammonia. The inside temperature rose briefly to 42° C., and the internal pressure rose to 6.0 bars. After the addition of ammonia was complete, the inside temperature dropped within 30 minutes to 20° C., as cooling was continued.

The reaction batch was prepared as in Example 1. By distillation of the excess ammonia, 64 kg of distillate (65% by weight ammonia, 35% by weight methylene chloride) were obtained. The n-propyl silazane solution (123 kg) obtained after filtration and washing of the precipitate, was clear and colorless and contained 3.79% by weight solids (determined by drying for one hour at 60° C.). The yield was thus 92% of theoretical.

For the evaluation of the film quality, 20 ml of this silazane were evaporated in an aluminum dish at room temperature. The resulting polysilazane film was uniformly smooth, transparent, and free of turbidities and other irregularities.

For further testing, the silazane solution was diluted with methylene chloride to 0.5% by weight and applied to a steel plate (60×60 mm) of 0.2 mm thickness. This yielded, after evaporation of the methylene chloride at room temperature, a film of about 4–6 μm thickness. This film was hardened in a drying cabinet for 20 minutes at 150° C. The film could not be removed with adhesive tapes after the grid cuts, and, when the steel plate was bent around a mandrel of 20 mm diameter, the film did not come off.

EXAMPLE 3

Following the procedure of Example 1, 5.0 kg of phenyltrichlorosilane in 100 liters of methylenechloride were reacted with 25 kg of ammonia. The inside temperature rose briefly to 37° C., and the internal pressure rose to 4.8 bar. After the addition of ammonia was complete, the inside temperature dropped back to 20° C. within 27 minutes. The reaction batch was prepared as in Example 1.

By distillation of the excess ammonia, 17 kg of distillate (54% by weight ammonia, 46% methylene chloride) were obtained. The phenylsilazane solution obtained (138 kg) after filtering and washing out the precipitate was clear and colorless and contained 2.05% by weight solids (determined by drying for one hour at 60° C.). The yield was thus 93% of theoretical.

For the evaluation of film quality, 20 ml of this silazane solution was evaporated in an aluminum dish at room temperature. The resulting polysilazane film was uniformly smooth, transparent, and free of turbidities and other irregularities.

For further testing, the solution was diluted with methylene chloride to 0.5% by weight, and applied to a steel plate (60×60 mm) of 0.2 mm thickness. This yielded, after evaporation of the methylene chloride at room temperature, a film of about 4–6 μm thickness. This film was hardened in a drying cabinet for 60 minutes at 100° C. The film could not be removed with adhesive tapes after the grid cuts and, when the plate was bent around a mandrel of 20 mm diameter, the film did not come off.

EXAMPLE 4

In accordance with the procedure of Example 1, a mixture of 2.5 kg of dimethyl dichlorosilane and 5.0 kg of methyl trichlorosilane in 100 l of methylene chloride was reacted with 30 kg of ammonia. The inside temperature rose briefly to 40° C., and the internal pressure rose to 5.5 bar. After the addition of ammonia was complete, the inside temperature dropped again within 30 minutes to 20° C. due to continued cooling. Subsequent to filtration and washing out of the precipitate, as in Example 1, 124 kg of silazane solution with 3.1% by weight solids were obtained (determined by drying for one hour at 60° C.).

For the evaluation of the film quality, 20 ml of this silazane solution were evaporated in an aluminum dish at room temperature. The resulting polysilazane film was uniformly smooth, transparent, and free of turbidities or other irregularities.

For further testing, the solution was diluted with methylene chloride to 0.5% by weight and applied to a steel plate (60×60 mm) of 0.2 mm thickness. This yielded a film of about 4 to 6 μm thickness after evaporation of the methylene chloride at room temperature. This film was hardened in a drying cabinet for 30 minutes at 80° C. After the grid cuts, the film could not be removed with adhesive tapes. Also, the film did not come off when the plate was bent around a mandrel of 20 mm diameter.

EXAMPLE 5

A three-liter autoclave of refined steel was charged with a solution of 50 g of methyltribromosilane in 400 ml of methylene chloride. Under stirring and water-cooling, 250 g of ammonia which had been first fed to and weighed in a small filling autoclave were pumped in within 10 minutes under ice cooling. During ammonolysis, the inside temperature rose briefly to 30° C., and the internal pressure rose to 3.2 bars. After the addition of ammonia was complete. The stirring was continued for four hours under water-cooling. The inside temperature dropped within 20 minutes to below 20° C.

After expansion and volatilization of the excess ammonia, the autoclave was opened and the reaction mixture was filtered through a fluted filter. The ammonium bromide precipitate was washed twice, each time with 100 ml of methylene chloride. The filtrate and the wash liquors were combined.

The methyl silazane solution thus obtained (420 g) was clear and colorless and contained 2.42% solids (determined by drying for one hour at 60° C.). The yield was thus 88% of theoretical.

The resulting polysilazane film was tested using the grid-cut and bending steps described above and was found to be suitable for use.

The Examples above show that a silazane solution produced according to the invention by ammonolysis with liquid ammonia under pressure at room temperature, yields a polysilazane film with excellent properties. However, a silazane solution prepared in a similar manner using the prior art procedure of ammonolysis with gaseous ammonia however, yields a film with unsuitable properties.

We claim:
1. In the process for the preparation of a condensable, film-forming organosilazane of formula $R_nSi(NH_2)_{4-n}$, wherein R represents a monovalent hydrocarbon radical and n is 1,2, or 3, by ammonolysis of an organohalosilane of formula $R_nSiX_{4-n}$, wherein R and n are as defined above and X is a halogen atom, with ammonia, the improvement comprising reacting a from about 5 to 15% by weight solution of the organohalosilane in inert solvent with excess liquid ammonia under pressure at temperatures of between 0° and 50° C.

2. The process of claim 1 wherein the liquid ammonia is present in an excess of at least three-fold by weight based on the weight of the organohalosilane.

3. The process of claim 2 wherein the liquid ammonia is present in an excess of from four to six-fold by weight.

4. The process of claim 1 wherein liquid ammonia is added to the solution of the organohalosilane.

5. The process of claims 1 or 4 wherein the liquid ammonia is diluted with an inert solvent.

6. The process of claim 1 wherein the ammonolysis takes place under stirring and the stirring is continued for from about 3 to 12 hours after the reactants are completely mixed.

7. The process of claim 1 wherein after the reaction is complete, excess ammonia is separated from the reaction mixture by evaporation and ammonium halide that is formed is separated from the reaction mixture by filtration.

8. The process of claim 7 wherein the filtrate free of excess ammonia and ammonium chloride is diluted with inert solvent.

9. The process of claim 1 wherein the organohalosilane is a compound of the formula $R_nSiCl_{4-n}$ wherein n is 1 or 2 and R, which may be the same or different, represents a linear or branched alkyl group having from 1 to 6 carbon atoms or a cyclohexyl, phenyl, or benzyl group, or mixtures thereof.

10. The process of claim 1 wherein methyl trichlorosilane or dimethyl trichlorosilane are reacted with liquid ammonia.

11. The process of claim 1 wherein more than one organohalosilane is reacted at the same time in the same solution.

12. The process of claim 1 wherein the inert solvent is selected from the group consisting of alicyclic or aliphatic hydrocarbon ethers having 4 to 8 carbon atoms, unsubstituted aromatic hydrocarbons having 6 to 8 carbon atoms, and chlorinated hydrocarbons having 1 to 6 carbon atoms.

* * * * *